United States Patent
Kuno et al.

(10) Patent No.: US 10,152,807 B2
(45) Date of Patent: Dec. 11, 2018

(54) SIGNAL PROCESSING FOR AN OPTICAL COHERENCE TOMOGRAPHY (OCT) APPARATUS

(71) Applicant: NIDEK CO., LTD., Gamagori, Aichi (JP)

(72) Inventors: Yuki Kuno, Gamagori (JP); Ai Takaya, Hamamatsu (JP); Naoki Takeno, Gamagori (JP)

(73) Assignee: NIDEK CO., LTD., Gamagori (JP)

( * ) Notice: Subject to any disclaimer, the term of this patent is extended or adjusted under 35 U.S.C. 154(b) by 0 days.

(21) Appl. No.: 15/182,057

(22) Filed: Jun. 14, 2016

(65) Prior Publication Data

US 2016/0371836 A1    Dec. 22, 2016

(30) Foreign Application Priority Data

Jun. 16, 2015   (JP) .................................. 2015-121574

(51) Int. Cl.

| | |
|---|---|
| *G06K 9/00* | (2006.01) |
| *G06T 11/00* | (2006.01) |
| *A61B 3/10* | (2006.01) |
| *G06T 7/50* | (2017.01) |

(52) U.S. Cl.
CPC ............ *G06T 11/008* (2013.01); *A61B 3/102* (2013.01); *G06T 7/50* (2017.01)

(58) Field of Classification Search
None
See application file for complete search history.

(56) References Cited

U.S. PATENT DOCUMENTS

| | | |
|---|---|---|
| 2011/0001929 A1 | 1/2011 | Tawada |
| 2011/0205490 A1 | 8/2011 | Murata et al. |
| | (Continued) | |

FOREIGN PATENT DOCUMENTS

| | | |
|---|---|---|
| JP | 2010-220772 A | 10/2010 |
| JP | 2011-010944 A | 1/2011 |
| | (Continued) | |

OTHER PUBLICATIONS

Lee, J. et al., "Motion correction for phase-resolved dynamic optical coherence tomography imaging of rodent cerebral cortex," Optics Express, Oct. 24, 2011, pp. 21258-21270, vol. 19, No. 22.

*Primary Examiner* — Idowu O Osifade
(74) *Attorney, Agent, or Firm* — Oliff PLC

(57) ABSTRACT

An OCT signal processing apparatus includes: a OCT signal receiver configured to receive a plurality of OCT signals detected by an OCT device based on measurement light radiated to a test substance and reference light; a display; a controller configured to: processes the plurality of OCT signals received by the OCT signal receiver to obtain 3-dimensional motion contrast data; extract depth region data from the 3-dimensional motion contrast data, the depth region data representing motion contrast data in a depth region of a part of the test substance; and display, on the display, a confirmation screen including the motion contrast image based on the depth region data to confirm quality of 3-dimensional motion contrast data obtained by processing the plurality of OCT signals which are temporally different from each other in the same region of the test substance.

17 Claims, 5 Drawing Sheets

(56) References Cited

U.S. PATENT DOCUMENTS

| | | | | |
|---|---|---|---|---|
| 2011/0299034 A1* | 12/2011 | Walsh | ............. | A61B 3/102 |
| | | | | 351/206 |
| 2012/0110065 A1* | 5/2012 | Oshima | ............. | G06F 3/1204 |
| | | | | 709/203 |
| 2013/0301000 A1* | 11/2013 | Sharma | ............. | A61B 3/102 |
| | | | | 351/206 |
| 2015/0092161 A1 | 4/2015 | Akita | | |
| 2015/0168127 A1* | 6/2015 | Takeno | ............. | G01B 9/02091 |
| | | | | 356/479 |

FOREIGN PATENT DOCUMENTS

| JP | 2011-172822 A | 9/2011 |
|---|---|---|
| JP | 2015-066242 A | 4/2015 |

* cited by examiner

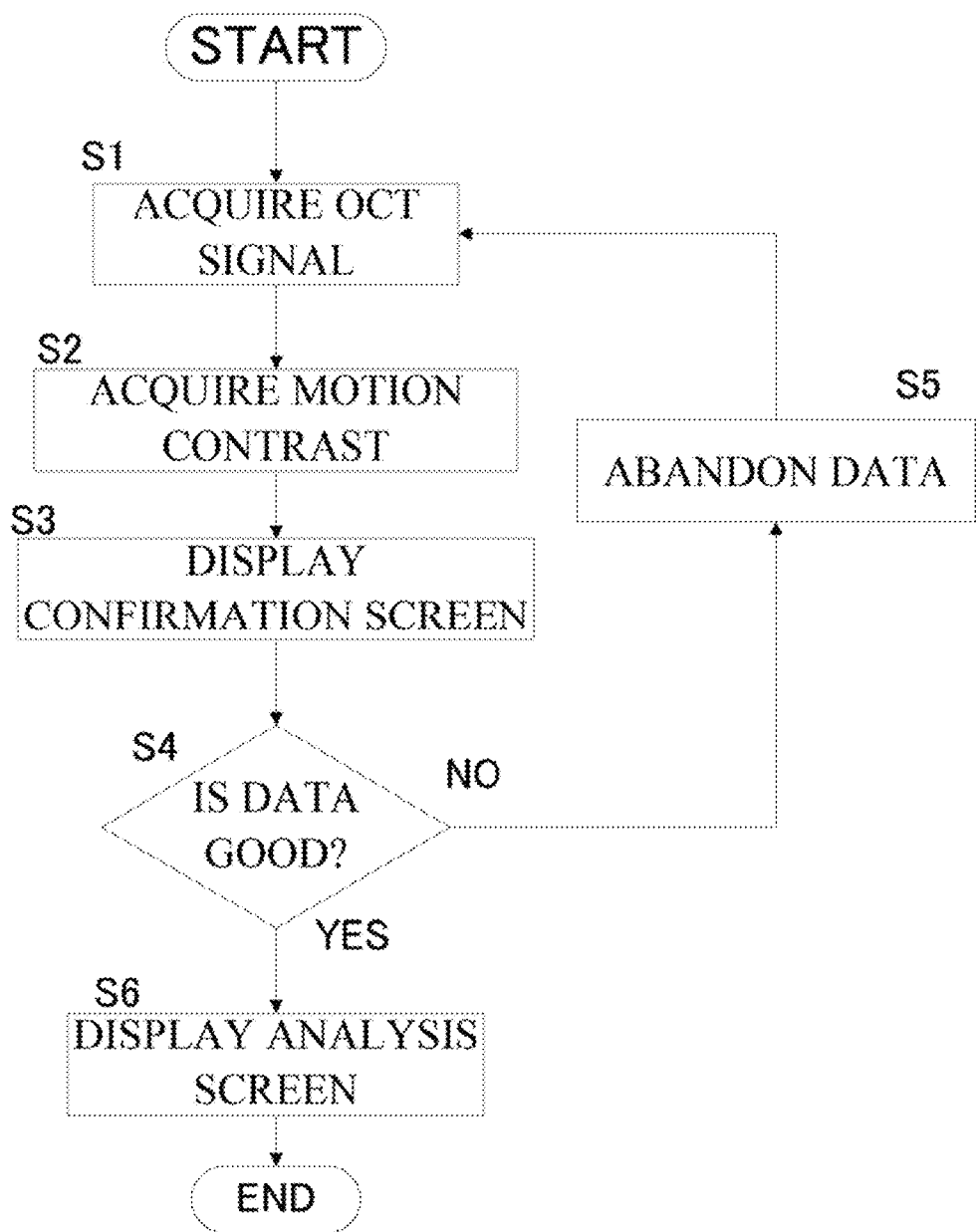

SIGNAL PROCESSING FOR AN OPTICAL COHERENCE TOMOGRAPHY (OCT) APPARATUS

CROSS REFERENCE TO RELATED APPLICATION

This application is based upon and claims the benefit of priority of Japanese Patent Application No. 2015-121574 filed on Jun. 16, 2015, the contents of which are incorporated herein by reference in its entirety.

BACKGROUND

The present disclosure relates to an OCT signal processing apparatus that processes an OCT signal of a test substance acquired by an OCT device, an OCT signal processing program, and an OCT apparatus.

In the related art, an apparatus that uses an optical coherence tomography (OCT) device is known as an apparatus capable of imaging tomographic images of a test substance (see Patent Document 1). The OCT device splits light emitted from a light source into measurement light and reference light and radiates the split measurement light to a tissue of the test substance. The OCT device combines the measurement light reflected from the tissue and the reference light and acquires an OCT signal of the combined light.

[Patent Document 1] JP-A-2011-172822
[Patent Document 2] JP-A-2010-220772
[Non-Patent Document 1] J. Lee, V. Srinivasan, H. Radhakrishnan, and D. a Boas, "Motion correction for phase-resolved dynamic optical coherence tomography imaging of rodent cerebral cortex.," Opt. Express, vol. 19, no. 22, pp. 21258 to 70 October 2011

SUMMARY

Incidentally, an apparatus that acquires a motion contrast (for example, a motion of an object such as a blood flow) using an OCT signal obtained by an OCT device has recently been proposed. An angiography image or the like is acquired by imaging the motion contrast.

In such an apparatus, for example, in a case in which a motion contrast image is not clear, there is a possibility of sufficient analysis not being conducted. In this case, it is necessary to image a test substance with an OCT device again, which involves a labor. However, in an apparatus of the related art, it is difficult to confirm quality of an imaged result when a motion contrast image is imaged.

The present disclosure is devised in view of the problem of the related art and an object of the present disclosure is to provide an OCT signal processing apparatus capable of appropriately confirming an imaged result, an OCT signal processing program, and an OCT apparatus.

An OCT signal processing apparatus includes:
an OCT signal receiver configured to receive a plurality of OCT signals detected by an OCT device based on measurement light radiated to a test substance and reference light, the plurality of OCT signals being temporally different from each other in the same region of the test substance;
a display;
a controller configured to:
process the plurality of OCT signals received by the OCT signal receiver to obtain 3-dimensional motion contrast data;
extract depth region data from the 3-dimensional motion contrast data, the depth region data representing motion contrast data in a depth region of a part of the test substance; and
display, on the display, a confirmation screen including the motion contrast image based on the depth region data to confirm quality of 3-dimensional motion contrast data obtained by processing the plurality of OCT signals.

A non-transitory computer readable recording medium stores an OCT signal processing program, when executed by a processor of an OCT signal processing apparatus including an OCT signal receiver configured to receive a plurality of OCT signals detected by an OCT device based on measurement light radiated to a test substance and reference light and a display, the plurality of OCT signals being temporally different from each other in the same region of the test substance, causing the OCT signal processing apparatus to execute:
processing the plurality of OCT signals received by the OCT signal receiver to obtain 3-dimensional motion contrast data;
extract depth region data from the 3-dimensional motion contrast data, the depth region data representing motion contrast data in a depth region of a part of the test substance;
display, on the display, a confirmation screen including the motion contrast image based on the depth region data to confirm quality of 3-dimensional motion contrast data obtained by processing the plurality of OCT signals.

An OCT apparatus includes:
an OCT optical system including a scanning unit configured to scan a test substance with measurement light, the OCT optical system acquiring a plurality of OCT signals based on measurement light scanned on a test substance by a scanning unit and reference light;
a display; and
a controller configured, when a release signal for starting imaging of the test substance by OCT optical system is received, to:
acquire the plurality of OCT signals which are temporally different from each other in the same region by controlling the scanning unit
process the plurality of OCT signals to obtain 3-dimensional motion contrast data;
extract depth region data from the 3-dimensional motion contrast data, the depth region data representing motion contrast data in a depth region of a part of the test substance;
display a confirmation screen including the motion contrast data on the display to confirm quality of the 3-dimensional motion contrast data.

BRIEF DESCRIPTION OF THE DRAWINGS

FIG. 3 is a flowchart illustrating a control operation according to the embodiment.

DESCRIPTION OF ILLUSTRATIVE EMBODIMENTS

Figure 1:
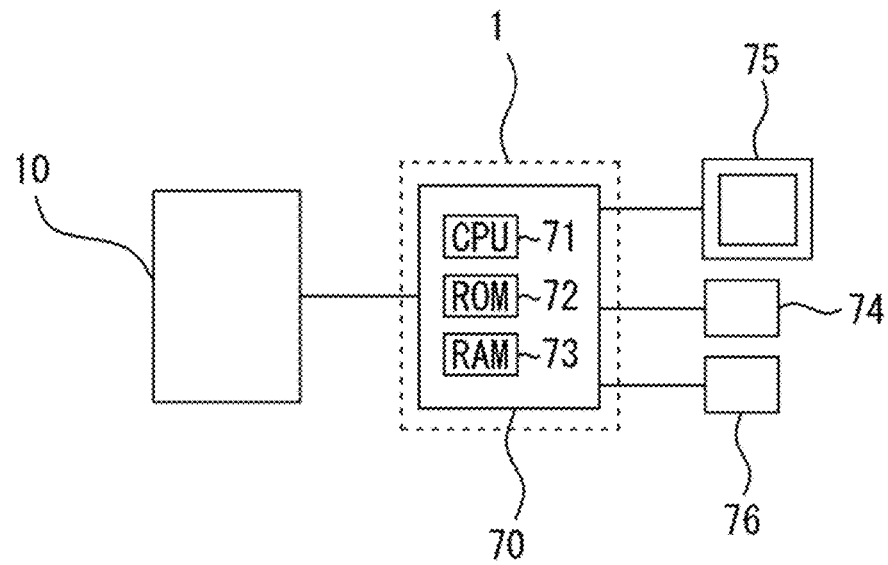
FIG. 1 is a block diagram illustrating an overview of an embodiment.

Hereinafter, an embodiment will be described in brief with reference to the drawings. An OCT signal processing apparatus (for example, an OCT signal processing apparatus 1 in FIG. 1) according to the embodiment processes an OCT signal acquired by, for example, an OCT device (for example, an OCT device 10).

The OCT signal processing apparatus mainly includes, for example, a controller (for example, a controller 70). For example, the controller displays a confirmation screen (for example, a confirmation screen 80) on a display unit (for example, a display unit 75). The confirmation screen is, for example, a screen for confirming quality of 3-dimensional motion contrast data. For example, the 3-dimensional motion contrast data is acquired by processing the OCT signal detected by the OCT device (the details will be described later). A motion contrast may be, for example, information obtained by comprehending a motion (for example, a blood flow or a tissue change) of an object.

For example, the OCT device detects an OCT signal based on the measurement light and the reference light scanning on a test substance. The OCT device may include, for example, a measurement light source (for example, a measurement light source 102), a light splitter (for example, a coupler 104), a reference optical system (for example, a reference optical system 110), a measurement optical system (for example, a measurement optical system 106), a scanning unit (for example, a scanning unit 108), and a light-receiving optical system (for example, a detector 120).

For example, the OCT device may be controlled by the controller of the OCT signal processing apparatus or may be controlled by a controller which is provided separately from the controller of the OCT signal processing apparatus.

For example, the controller may display a motion contrast image based on depth region data on the confirmation screen. Accordingly, a tester can confirm the quality of motion contrast data in a depth region of a part of the test substance. Accordingly, it is possible to appropriately confirm the entire 3-dimensional motion contrast data.

The depth region data is, for example, 3-dimensional motion contrast data which is extracted from the depth region of a part of the test substance. For example, the depth region data may be 3-dimensional data obtained by extracting a part of the 3-dimensional motion contrast data or may be 2-dimensional data obtained by extracting a part of the 3-dimensional motion contrast data.

For example, the depth region may be a region based on a retina layer of a fundus or may be a region based on a layer in which blood vessels of a fundus are compact. For example, the depth region may be a region in which measurement light spreads in a scanning direction or may be a region which is specified by the position of measurement light in an optical axis (for example, a depth direction or a z direction) at each scanning position. For example, the depth region may also be a planar region or may be a curved region. For example, the depth region may be a region which has a width (for example, a depth or a thickness) in the depth direction or may be a region which has no width. For example, the depth region may be expressed as a layer region.

For example, the controller may acquire a motion contrast image from the OCT device or may generate a motion contrast image based on the 3-dimensional motion contrast data acquired from the OCT device. Of course, the controller may calculate the 3-dimensional motion contrast data based on the OCT signal acquired from the OCT device. For example, the 3-dimensional motion contrast data is acquired by performing a calculation process on a plurality of OCT signals acquired at different timing with respect to the same region.

The controller may display the plurality of motion contrast images on the confirmation screen so that the motion contrast images are switchable. For example, the plurality of motion contrast images may be images that are generated for every piece of a plurality of depth region data. In this case, the plurality of pieces of depth region data may be pieces of motion contrast data extracted in a plurality of depth regions with different depths, respectively. Accordingly, the tester can confirm the motion contrast data in the depth regions with different depths, and thus can confirm the quality of the motion contrast data more appropriately.

The controller may arrange and display the plurality of motion contrast images on the confirmation screen. Accordingly, the tester can easily compare the pieces of motion contrast data in the plurality of depth regions with different depths.

The controller may display a motion contrast image in a depth region in which a lesion is contained on the confirmation screen. In this case, the controller may specify the depth region in which the lesion is contained based on the 3-dimensional motion contrast data. For example, the controller may detect the lesion based on the 3-dimensional motion contrast data and specify the depth region in which the detected lesion is contained. Accordingly, the tester can easily confirm whether the motion contrast data of a lesion portion is clearly acquired.

The controller may display a motion contrast image in a specific depth region based on relevant information on the confirmation screen. The relevant information may be, for example, information regarding a medical history of a patient, an imaging condition, or the like. For example, the controller may acquire relevant information from the OCT device, a storage unit (for example, a storage unit 74), or the like. Accordingly, it is possible to reduce a labor for designating a depth region of the motion contrast image displayed on the confirmation screen.

Of course, the controller may display a motion contrast image in a preset depth region on the confirmation screen.

The controller may switch a display magnification of the motion contrast image displayed on the confirmation screen. For example, the controller may switch the display magnification used at the time of displaying of the motion contrast image on the confirmation screen from a first display magnification to a second display magnification which is different from the first display magnification. Accordingly, for example, the tester can confirm the quality of the 3-dimensional motion contrast more accurately by observing the expanded and displayed motion contrast image. Of course, the controller may arrange and display a plurality of motion contrast images with mutually different display magnifications on the confirmation screen.

The controller may sequentially display the motion contrast images on the confirmation screen from pixel lines corresponding to acquired scanning lines. Accordingly, the tester can confirm the quality of the 3-dimensional motion contrast data before the acquisition of the 3-dimensional motion contrast data is completed. Accordingly, in a case in which an artifact (for example, an unnecessary signal which is not related to the structure of the test substance) occurs halfway, re-imaging can be executed at that time point.

The controller may display an index for evaluating the quality of the 3-dimensional motion contrast data on the confirmation screen. Accordingly, the tester can quantitatively comprehend the quality of the 3-dimensional motion contrast data. The index may also be, for example, an index indicating clearness of the 3-dimensional motion contrast data.

The controller may display an index calculated for each of the plurality of depth region data on the confirmation screen. For example, the controller may display at least one of the plurality of indexes calculated for the plurality of pieces of depth region data on the confirmation screen. Accordingly, the indexes in the different depth regions can be compared. Of course, the controller may display an index calculated for all the pieces of 3-dimensional motion contrast data on the confirmation screen. For example, the controller may display an index of all layers obtained by collectively calculating the plurality of depth regions on the confirmation screen.

The index for evaluating the 3-dimensional motion contrast data may be, for example, a ratio of an integrated value of intensity images to an integrated value of the motion contrast images. In a case in which this ratio is calculated, a ratio between both of the integrated values in a one certain scanning line may be the index or a ratio between both of the integrated values in a plurality of scanning lines may be the index. For example, there is an artifact, the foregoing index decreases. Accordingly, in a case in which the index is small, the tester may determine that the 3-dimensional motion contrast data is not appropriate. In a case in which the index is large, the tester may determine that the 3-dimensional motion contrast data is appropriate.

The index may be a correlation value between intensity images or may be a correlation value between a plurality of OCT signals when a motion contrast image is generated. In accordance with such a correlation value, for example, the degree of deviation in a subject's eye is evaluated when the measurement light is scanned in the same scanning line of the test substance a plurality of times. For example, as the correlation value is closer to 1, it is determined that the correlation is higher and the deviation in the subject's eye is smaller. Accordingly, the tester can confirm the extent of the artifact occurring due to the deviation in the subject's eye by confirming the correlation value.

For example, the index may be calculated based on a plurality of OCT signals which are temporally different from each other with respect to the same region to generate the motion contrast image. In this case, the controller may calculate the index based on a motion contrast obtained by processing the plurality of OCT signals.

The controller may display a part of the analysis result on the confirmation screen. For example, the controller may display the part of the analysis result on the confirmation screen and may further display the remaining analysis result on an analysis screen. For example, an analysis result in which a processing time is short may be displayed on the confirmation screen and an analysis result in which the processing time is long may be displayed on the analysis screen. Accordingly, the tester can determine the quality of the 3-dimensional motion contrast data at a time point at which the tester confirms the part of the analysis result displayed on the confirmation screen. Accordingly, the tester can determine the re-imaging without confirming the analysis result in which the processing time is long on the analysis screen.

The controller may display an enface image based on the depth region data on the confirmation screen. Here, an enface may be a surface horizontal to the surface of a fundus or a 2-dimensional horizontal tomographic surface of a fundus.

The controller may receive an operation signal output from an operation unit (for example, an operation unit 76) operated by the tester. In this case, for example, the controller may output a re-imaging signal based on an operation signal received when the tester displays the confirmation screen. The re-imaging signal is, for example, a signal for acquiring the 3-dimensional motion contrast data again by processing the plurality of OCT signals which are temporally different from each other with respect to the same region detected again by the OCT device.

Accordingly, in the OCT signal processing apparatus according to the embodiment, for example, the controller may receive an operation signal output from the operation unit operated by the tester and output a re-imaging signal for again acquiring the 3-dimensional motion contrast data obtained by processing the plurality of OCT signals detected again at different timing by the OCT device based on an operation signal received at the time of displaying of the confirmation screen.

The controller may store the 3-dimensional motion contrast data which serves as a basis of the motion contrast image displayed on the confirmation screen in the storage unit or may delete the 3-dimensional motion contrast data without storing the 3-dimensional motion contrast data in the storage unit based on the operation signal received from the operation unit at the time of displaying of the confirmation screen. For example, the tester may determine the quality of the 3-dimensional motion contrast data on the confirmation screen and may use the operation unit to perform an input regarding whether the 3-dimensional motion contrast data is stored in the storage unit or deleted.

Accordingly, in the OCT signal processing apparatus according to the embodiment, for example, the controller may receive an operation signal output from the operation unit operated by the tester and may determine to store the 3-dimensional motion contrast data in the storage unit or delete the 3-dimensional motion contrast data based on the operation signal received at the time of displaying of the confirmation screen.

The controller may display the confirmation screen, and then may display the analysis screen for displaying the analysis result of the 3-dimensional motion contrast data on the display unit. For example, the controller may switch display from the confirmation screen to the analysis screen based on the operation signal received from the operation unit after the confirmation screen is displayed. For example, based on the operation signal, the controller may store the 3-dimensional motion contrast data in the storage unit, and then display the 3-dimensional motion contrast data on the analysis screen.

Accordingly, in the OCT signal processing apparatus according to the embodiment, for example, the controller may display the confirmation screen, and then may display the analysis screen for analyzing the 3-dimensional motion contrast data.

The controller may display the confirmation screen on the display unit based on a release signal for imaging the subject's eye by the OCT device. In this case, the controller may start acquiring the OCT signal by the OCT device based on the release signal. For example, the controller may cause the scanning unit to perform scanning based on the release signal. For example, the controller may process a plurality of OCT signals which are temporally different from each other with respect to the same region based on the release signal and acquire the 3-dimensional motion contrast data. For example, the controller may display the motion contrast image based on the depth region data extracted in the depth region of a part of the test substance among the pieces of 3-dimensional motion contrast data on the confirmation screen.

The controller may include a processor (for example, a CPU 71) and storage units (for example, a ROM 72 and a storage unit 74). The processor may execute the OCT signal processing apparatus to execute an OCT signal processing program stored in the storage unit. For example, the OCT signal processing program may include a display control step. The display control step may be, for example, a step of displaying the enface image based on the above-described depth region data on the confirmation screen.

EMBODIMENT

Hereinafter, an OCT signal processing apparatus according to an embodiment will be described with reference to the drawings. An OCT signal processing apparatus 1 illustrated in FIG. 1 processes an OCT signal acquired by an OCT device 10.

The OCT signal processing apparatus 1 includes, for example, a controller 70. The controller 70 is realized by, for example, a general central processing unit (CPU) 71, a ROM 72, and a RAM 73. The ROM 72 stores, for example, an OCT signal processing program for processing the OCT signal, various programs for controlling an operation of the OCT device 10, and initial values. The RAM 73 temporarily stores, for example, various kinds of information. The controller 70 may be configured to include a plurality of controllers (that is, a plurality of processors).

As illustrated in FIG. 1, for example, a storage unit (for example, a nonvolatile memory) 74, an operation unit 76, and a display unit 75 are electrically connected to the controller 70. The storage unit 74 is, for example, a non-transient storage medium that can retain storage content even when supply of power is cut off. For example, a hard disk, a flash ROM, a detachably mounted USB memory can be used as the storage unit 74.

Various operation instructions are input to the operation unit 76 by the tester. The operation unit 76 outputs a signal according to an input operation instruction to the CPU 71. In the operation unit 76, for example, at least one of the user interfaces such as a mouse, a joystick, a keyboard, and a touch panel may be used.

The display unit 75 may be a display which is mounted on the body of the apparatus 1 or may be display which is connected to the body. For example, a display of a person computer (hereinafter referred to as a "PC") may be used. A plurality of displays may be used together. The display unit 75 may be a touch panel. In a case in which the display unit 75 is a touch panel, the display unit 75 may also be used as the operation unit 76. The display unit 75 displays, for example, an OCT image, a motion contrast image, and the like acquired by the OCT device 10.

The OCT device 10 is connected to, for example, the OCT signal processing apparatus 1 according to the embodiment. A connection method may be a wireless method, a wired method, or both of the wireless and wired methods. The OCT signal processing apparatus 1 may be configured to be integrated and received in the same casing along with, for example, the OCT device 10 or may be configured to be separated. The controller 70 acquires at least one piece of OCT data of an OCT signal, motion contrast data, and an enface image from the connected OCT device 10. Of course, the controller 70 may not be connected to the OCT device 10. In this case, the controller 70 may acquire the OCT data imaged by the OCT device 10 via a storage medium.

OCT Device

Figure 2:
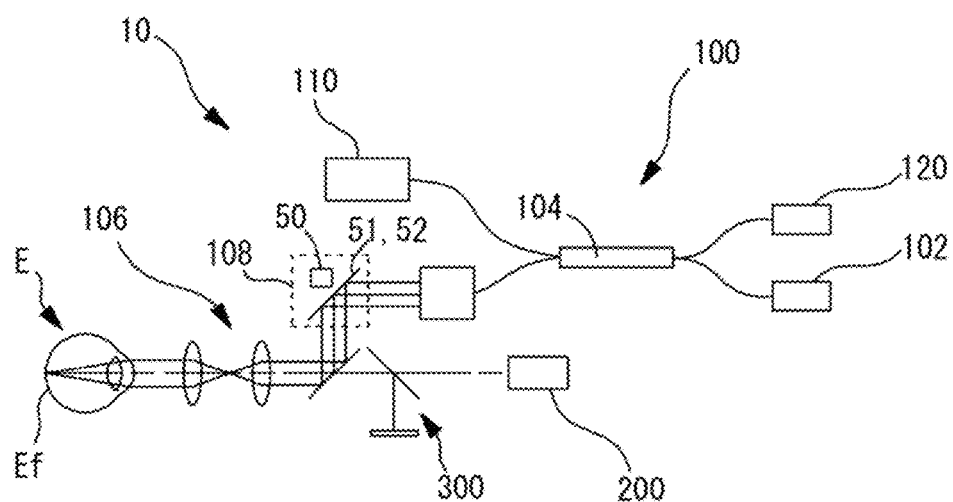
FIG. 2 is a diagram illustrating an example of an optical system of an OCT device.

Hereinafter, an overview of the OCT device 10 will be described with reference to FIG. 2. For example, the OCT device 10 radiates measurement light to a subject's eye E and acquires an OCT signal acquired by the measurement light and its reflected light. The OCT device 10 mainly includes, for example, an OCT optical system 100.

OCT Optical System

The OCT optical system 100 radiates measurement light to the subject's eye E and detects an interference signal between its reflected light and the reference signal. The OCT optical system 100 mainly includes, for example, a measurement light source 102, a coupler (light splitter) 104, a measurement optical system 106, a reference optical system 110, and a detector 120.

The OCT optical system 100 is an optical system of a so-called optical coherence tomography (OCT). In the OCT optical system 100, the coupler 104 splits light emitted from the measurement light source 102 into measurement light (sample light) and reference light. The split measurement light is guided to the measurement optical system 106 and the reference light is guided to the reference optical system 110. The measurement light is guided to a fundus Ef of the subject's eye E via the measurement optical system 106. Thereafter, the interference light by combination of the reference light and the measurement light reflected by the subject's eye E is received by the detector 120.

The measurement optical system 106 includes, for example, a scanning unit (for example, an optical scanner) 108. For example, the scanning unit 108 changes a scanning position of the measurement light on the subject's eye to change an imaging position on the subject's eye. For example, the CPU 71 controls an operation of the scanning unit 108 based on set scanning position information and acquires the OCT signal based on a light-receiving signal detected by the detector 120.

For example, the scanning unit 108 scans the measurement light in XY directions (transverse direction) on the fundus. The scanning unit 108 is disposed at a position substantially conjugated with a pupil. For example, the scanning unit 108 includes two galvanometer mirrors 51 and 52 and reflection angles of the galvanometer mirrors are adjusted as any angles by a driving mechanism 50. Accordingly, a reflection (traveling) direction of a light flux emitted from the light source 102 is changed and the light flux is scanned in any direction on the fundus. That is, "B scanning" is performed on the fundus Ef. The scanning unit 108 may have a configuration in which light is deflected. For example, in addition to reflection mirrors (a galvanometer mirror, a polygon mirror, and a resonant scanner), an acoustic optical element (AOM) that changes a traveling (deflection) direction of light is used.

The reference optical system 110 generates reference light which is combined with reflected light acquired by reflecting the measurement light in the fundus Ef. The reference optical system 110 may be of a Michelson type or may be of a Mach-Zehnder type. For example, the reference optical system 110 returns light formed by a reflection optical system (for example, a reference mirror) and coming from the coupler 104 again to the coupler 104 by reflecting the light from the reflection optical system and guides the light to the detector 120. As another example, the reference optical system 110 transmits light formed by a transmission optical system (for example, an optical fiber) and coming from the coupler 104 without returning the light and guides the light to the detector 120.

For example, the reference optical system 110 has a configuration in which a difference between optical paths of the measurement light and the reference light is changed by moving an optical member located in a reference optical path. For example, the reference mirror is moved in an optical axis direction. The configuration for changing the difference between the optical paths may be disposed in an optical path of a light-guiding optical system 106.

The detector 120 detects an interference state of the measurement light and the reference light. In a case of a Fourier domain OCT, a spectrum intensity of reference light is detected by the detector 120 and a depth profile (A scanning signal) in a predetermined range is acquired through Fourier transform on spectrum intensity data.

As the OCT device 10, for example, a spectral-domain OCT (SD-OCT), a swept-source OCT (SS-OCT), or a time-domain OCT (TD-OCT) may be used.

In the case of the SD-OCT, a low coherent light source (wideband light source) is used as the light source 102. In the detector 120, a spectroscopic optical system (spectrometer) that diffracts the interference light into respective frequency components (wavelength components) is installed. The spectroscopic system is formed by, for example, a diffraction grating and a line sensor.

In the case of the SS-OCT, a wavelength scanning type light source (wavelength variable light source) that changes an emitting wavelength temporally at a high speed is used as the light source 102 and, for example, a single light-receiving element is installed as the detector 120. The light source 102 is configured by, for example, a light source, a fiber ring resonator, and a wavelength selection filter. For example, a combination of a diffraction grating and a polygon mirror or a filter using a Fabry-Perot etalon can be exemplified as the wavelength selection filter.

Front Imaging Optical System

For example, a front imaging optical system 200 images the fundus Ef of the subject's eye E in a front direction (for example, an optical axis direction of the measurement light) to obtain a front image of the fundus Ef. The front imaging optical system 200 may include a second scanning unit that 2-dimensionally scans the measurement light (for example, infrared light) emitted from the light source on the fundus and a second light-receiving element that receives fundus-oculi reflected light via a confocal opening disposed at a position substantially conjugated with the fundus, and has an apparatus configuration of a so-called scanning laser ophthalmoscope (SLO) (for example, see JP-A-2015-66242). A configuration of a so-called fundus-oculi camera type may be used as the configuration of the front imaging optical system 200 (see JP-A-2011-10944). The front imaging optical system 200 according to the embodiment is also used as an optical element of a part of the measurement optical system 106.

Fixation Target Projection Unit

A fixation target projection unit 300 includes an optical system that guides a visual line direction of the eye E. The projection unit 300 has a fixation target which is presented to the eye E and can guide the eye E in a plurality of directions.

For example, the fixation target projection unit 300 has a visible light source that emits the visible light and changes a presentation position of a target 2-dimensionally. Accordingly, the visual line direction is changed and a part to be imaged is consequently changed. For example, when a fixation target is presented in the same direction as an imaging optical axis, a central portion of the fundus is set as a part to be imaged. When the fixation target is presented above the imaging optical axis, an upper portion of the fundus is set as a part to be imaged. That is, a part to be imaged is changed according to the position of a target with respect to the imaging optical axis.

For example, the fixation target projection unit 300 is considered to have various configurations such as a configuration in which a fixation position is adjusted using a lighting position of an LED arrayed in a matrix form and a configuration in which a fixation position is adjusted through lighting control of a light source by scanning light from the light source using an optical scanner. The fixation target projection unit 300 may be a type of an internal fixation lamp or may be a type of an external fixation lamp.

Control Operation

A control operation when OCT data acquired by the OCT device 10 is processed in the OCT signal processing apparatus 1 described above will be described with reference to the flowchart of FIG. 3. For example, the OCT signal processing apparatus 1 according to the embodiment processes an OCT signal detected by the OCT device 10 to acquire a motion contrast.

(Step S1)

Acquiring OCT Signal

First, the OCT signal processing apparatus 1 acquires the OCT signal. For example, the CPU 71 acquires the OCT signal detected by the OCT device 10 and stores data of the OCT signal in the storage unit 74 or the like. In the following description, for example, the CPU 71 controls the OCT device 10 to acquire the OCT signal. A controller may be installed separately from the OCT device 10.

Hereinafter, a method in which the OCT signal is detected by the OCT device 10 will be described. For example, the CPU 71 controls the fixation target projection unit 300 to project a fixation target to a test substance. The CPU 71 controls a driving unit (not illustrated) such that a measurement optical axis comes to the center of the pupil of the subject's eye E based on an anterior ocular segment observation image imaged with a camera (not illustrated) for anterior ocular segment observation and automatically performs alignment.

Figure 4A:
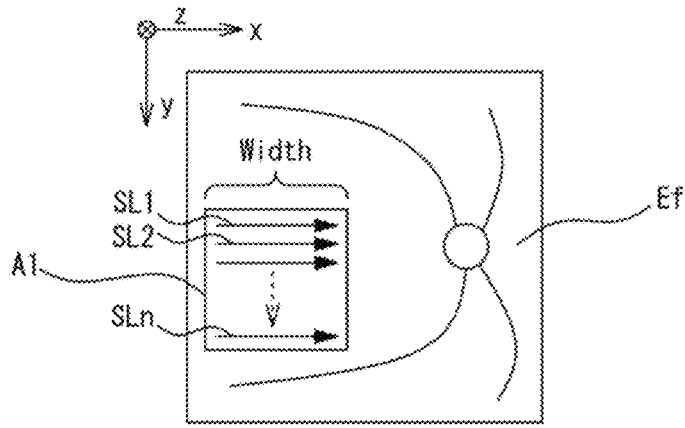
FIGS. 4A to 4C are diagrams illustrating acquisition of a motion contrast.

When the alignment is completed, the CPU 71 controls the OCT device 10 to image the subject's eye E. For example, the CPU 71 scans the measurement light in the fundus Ef. For example, as illustrated in FIG. 4A, the CPU 71 controls driving of the scanning unit 108 and scans the measurement light in a region A1 on the fundus Ef. In FIG. 4A, the direction of the z axis is set as the direction of an optical axis of the measurement light. The direction of the x axis is vertical to the z axis and is the horizontal direction of the test substance. The direction of the y axis is vertical to the z axis and is the vertical direction of the test substance.

For example, the CPU 71 scans the measurement light in the x direction along scanning lines SL1, SL2, . . . , and SLn in the region A1. Scanning the measurement light in a direction (for example, the x direction) intersecting the optical axis direction of the measurement light is referred to as "B scanning". An OCT signal obtained through the B scanning performed once is referred to as an OCT signal of one frame for description. The CPU 71 acquires the OCT signal detected by the detector 120 while the measurement light is scanned. For example, the CPU 71 stores the OCT signal acquired in the region A1 in the storage unit 74. The region A1 may be a scanning region in the xy directions, as described above, and may be scanning region in which a plurality of scanning lines in the x direction are arranged in the y direction. Accordingly, for example, the CPU 71 obtains the A scanning signal in the z direction at each scanning position by 2-dimensionally scanning the measurement light in the xy directions. That is, the CPU 71 acquires, for example, 3-dimensional data.

In the embodiment, the motion contrast is acquired based on the OCT signal. The motion contrast may be, for example, information obtained by comprehending a change in a blood flow, a retina tissue, or the like of the subject's eye. In a case in which the motion contrast is acquired, the CPU 71 acquires at least two OCT signals which are temporally different with respect to the same region of the subject's eye. For example, the CPU 71 performs the B scanning a plurality of times by spacing a time interval in each scanning line and acquires the plurality of OCT signals which are temporally different from each other. For example, the CPU 71 performs first B scanning at a certain time, and then performs second B scanning in the same scanning line as the first B scanning after a predetermined time has passed. The CPU 71 may acquire the plurality of OCT signals which are temporally different from each other by acquiring the OCT signals detected at that time by the detector 120.

Figure 4B:
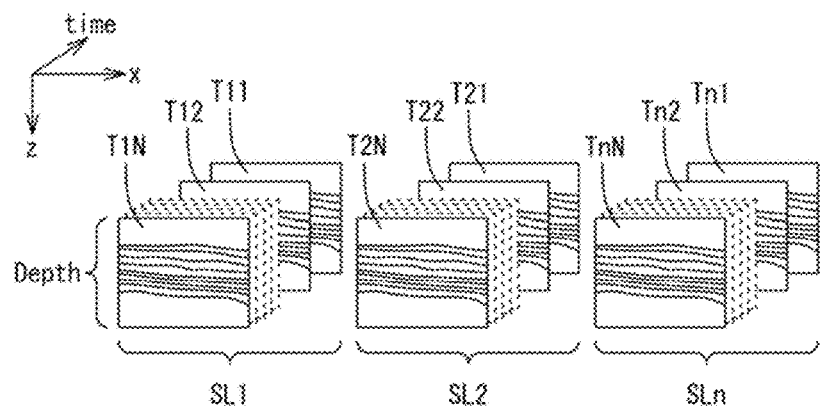

For example, FIG. 4B illustrates the OCT signals acquired in a case in which the B scanning is performed a plurality of times at different timing in the scanning lines SL1, SL2, . . . , and SLn. For example, FIG. 4B illustrates a case in which the scanning line SL1 is scanned at times T11, T12, . . . , and T1N, the scanning line SL2 is scanned at times T21, T22, . . . , and T2N, and the scanning line SLn is scanned at times Tn1, Tn2, . . . , and TnN. In this way, the CPU 71 may acquire the plurality of OCT signals which are temporally different from each other by controlling the OCT device 10 and performing the B scanning a plurality of times at different times in each scanning line. For example, the CPU 71 acquires the plurality of OCT signals which are temporally different from each other with respect to the same position and stores data of the plurality of OCT signals in the storage unit 74.

(Step S2)

Acquiring Motion Contrast

When The CPU 71 acquires the OCT signal, as described above, the CPU 71 processes the OCT signal to acquire the motion contrast. As a method of calculating the OCT signal to acquire the motion contrast, for example, a method of calculating an intensity difference between complex OCT signals, a method of calculating a phase difference between complex OCT signals, a method of calculating a vector difference between complex OCT signals, a method of multiplying a phase difference by a vector difference between complex OCT signals, and a method of using correlation between signals (correlation mapping) can be exemplified. In the embodiment, the method of calculating a phase difference as a motion contrast will be described as an example.

For example, in a case in which a phase difference is calculated, the CPU 71 performs Fourier transform on the plurality of OCT signals. For example, when a signal at the position of an n-th (x, z) in N frames is denoted by An (x, z), the CPU 71 obtains a complex OCT signal An (x, z) through the Fourier transform. The complex OCT signal An (x, z) contains a real number component and an imaginary number component.

Figure 4C:
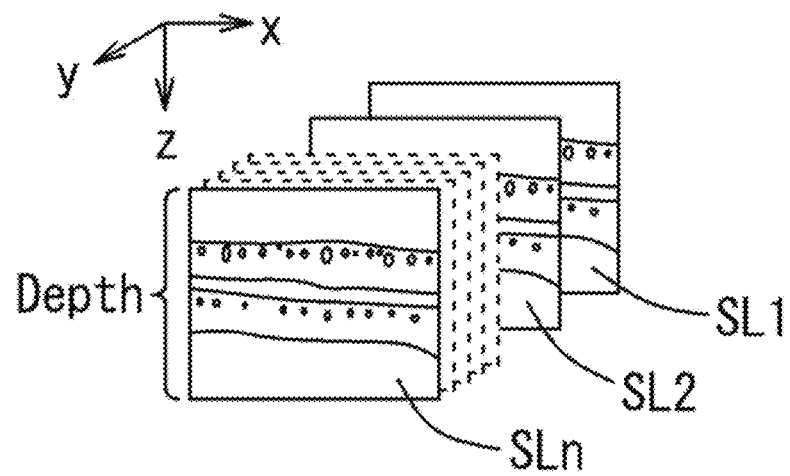

The CPU 71 calculates a phase difference between the complex OCT signals An (x, z) acquired at least at two different timing of the same position. For example, the CPU 71 calculates the phase difference using the following Formula (1). For example, the CPU 71 may calculate the phase difference in each scanning line (see FIG. 4C) and stores data of the phase difference in the storage unit 74. In the formula, An indicates a signal acquired at a time TN and * indicates a complex conjugate.

[Math. 1]

$$\Delta\Phi_n(x,z) = \arg(A_{n+1}(x,z) \times A_n^*(x,z)) \quad (1)$$

As described above, the CPU 71 acquires the 3-dimensional motion contrast data of the subject's eye E based on the OCT signal. As described above, the motion contrast is not limited to the phase difference, but an intensity difference, a vector difference, or the like may be acquired.

(Step S3)

Displaying Confirmation Screen

Figure 5A:
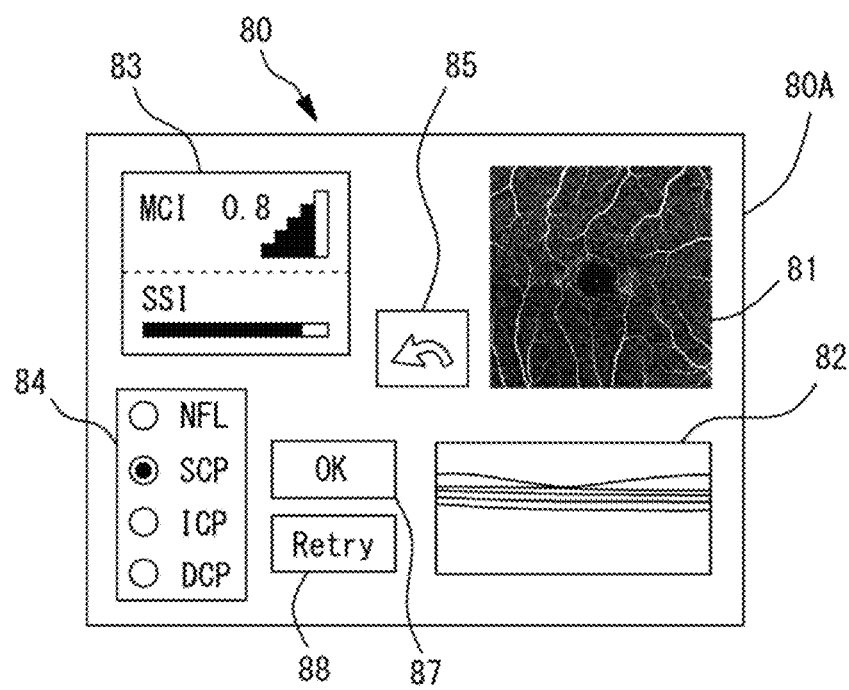
FIGS. 5A and 5B are diagrams illustrating an example of a display screen according to the embodiment.
Figure 5B:
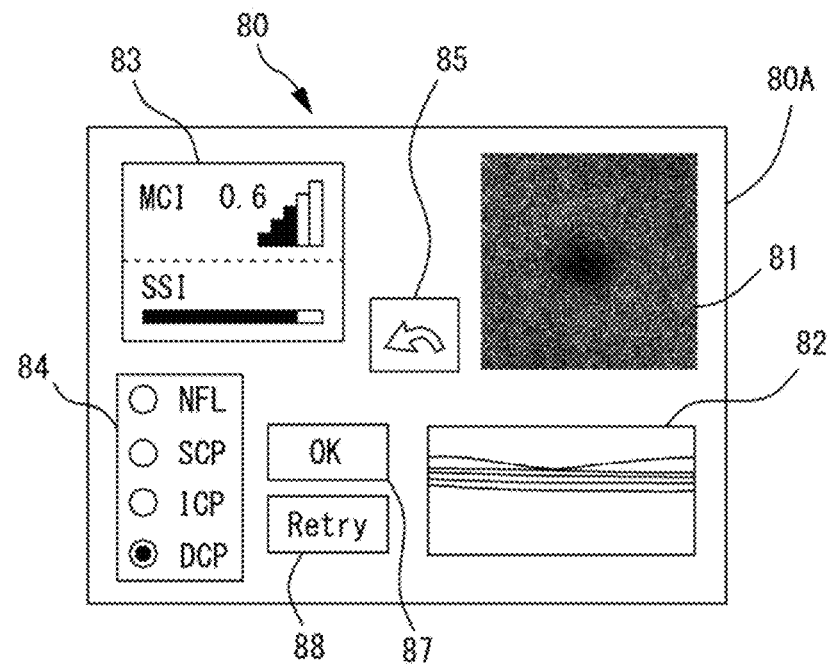

When a subject's eye is imaged, the CPU 71 displays, for example, a confirmation screen 80 illustrated in FIGS. 5A and 5B on the display unit 75. The confirmation screen 80 is a screen for confirming quality of motion contrast data (hereinafter abbreviated to MC data). For example, the CPU 71 displays a first display region 81, a second display region 82, a third display region 83, a first switch portion 84, and a second switch portion 85 on a confirmation screen 80A (see FIG. 5A).

First Display Region

The first display region 81 is a region in which a motion contrast image (hereinafter abbreviated to an MC image) is displayed. For example, the CPU 71 displays the MC image of any depth region in the first display region 81. In a case in which the fundus Ef of the subject's eye E is imaged by the OCT device 10 as in the embodiment, the MC image is observed as an angiography image (so-called OCT angiography image). For example, the MC image may be a 3-dimensional motion contrast image (hereinafter abbreviated to a 3-dimensional MC image) or may be a motion contrast front image (hereinafter abbreviated to an MC front image). Here, the front image may be a so-called enface image. An enface is, for example, a surface horizontal to the surface of a fundus or a 2-dimensional horizontal tomographic surface of a fundus.

As a method of generating the MC front image from the 3-dimensional MC data, for example, a method of extracting the MC data at least at a certain depth region in a depth direction can be exemplified. In this case, the MC front image may be generated using a profile of the MC data at least in the partial depth region.

First Switch Portion

The first switch portion 84 is an interface used to designate a depth region of the MC image displayed in the first display region 81. The first switch portion 84 may be, for example, a check box (see FIGS. 5A and 5B), a button, or a slider. For example, the first switch portion 84 may be configured such that a depth region is switched for each retina layer such as a nerve fiber layer (NFL), a ganglion cell layer (GCL), a retinal pigment epithelium (RPE), and a choroid. The first switch portion 84 may be configured such that a depth region is switched to a superficial capillary plexus (SCP), an intermediate capillary plexus (ICP), or a deep capillary plexus (DCP) based on a distribution of blood vessels. Of course, the depth region is not limited to the foregoing layers, but the first switch portion 84 may also be configured such that the depth region is switched to a depth region set from a boundary of retina layers within a predetermined range or a depth region set uniquely by the tester. The depth region may also be, for example, a region in which a plurality of retina layers are combined.

For example, the CPU 71 displays the MC image in a depth region designated in the first switch portion 84 in the first display region 81. For example, the CPU 71 segments the MC data into a plurality of depth regions through a segmentation process, extracts the MC data in the depth region designated in the first switch portion 84 among the segmented depth regions, and displays the MC data in the first display region 81.

In a case in which the depth regions are segmented through the segmentation process, for example, the CPU 71 may segment a depth region based on a boundary of the retina layers detected through edge detection of an intensity image or may segment a depth region based on a distribution of blood vessels detected from the MC image. Here, the intensity image is, for example, an image in which a luminance value is decided according to the intensity of an OCT signal.

FIG. 5A illustrates a state of the confirmation screen 80A when the SCP is designated in the first switch portion 84. In this case, thick blood vessels near the SCP are mainly confirmed in the MC image displayed in the first display region 81. On the other hand, FIG. 5B illustrates a state of the confirmation screen 80A when the DCP is designated in the first switch portion 84. In this case, thin blood vessels near the DCP are mainly observed in the MC image displayed in the first display region 81. In this way, the CPU 71 can switch the depth of the depth region of the MC image which is displayed in the first display region 81. Accordingly, it is possible to confirm the quality of the MC data for each of the depth regions in which depths are different.

Second Switch Portion 85

Figure 6:
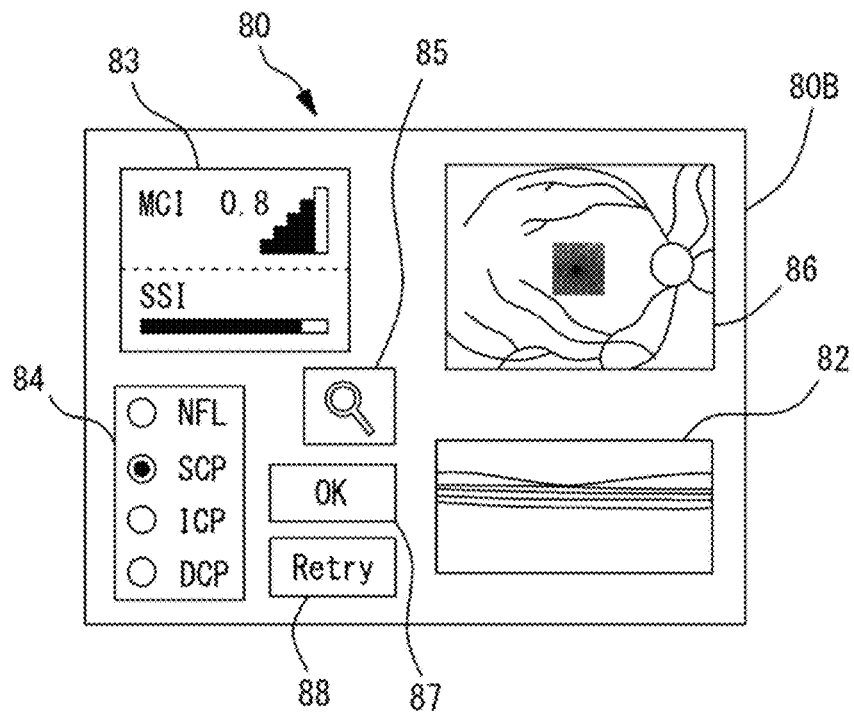
FIG. 6 is a diagram illustrating an example of a display screen according to the embodiment.

The second switch portion 85 is an interface used to switch between the confirmation screen 80A and a confirmation screen 80B (see FIG. 6). When the second switch portion 85 is operated, the CPU 71 switches the confirmation screen between the confirmation screens 80A and 80B. The second switch portion 85 may be, for example, a button or a check box.

Second Display Region

The second display region 82 is a region in which an intensity image based on the intensity of an OCT signal is displayed. In the second display region 82, for example, an intensity image of any one line on a map is displayed. For example, the CPU 71 may switch an image between the intensity image and the MC image and display the image in the second display region 82, or display the image in an overlapping manner. According to the depth region designated in the first switch portion 84, a region corresponding to the intensity image displayed in the second display region 82 may be emphasized or displayed by a line, filling, or the like.

Third Display Region

The third display region 83 is a region in which an index (motion contrast index: MCI) indicating clearness of the MC image is displayed. For example, the CPU 71 may display a numerical value or a graphic as the MCI in the third display region 83. The tester can determine the quality of the MC data with reference to the index. The CPU 71 may automatically perform re-imaging using the MCI as a standard. In this case, the MCI may not be displayed in the third display region 83.

As expressed in Formula (2), the MCI may be, for example, a ratio of an integrated value of the intensity image to an integrated value of the MC image in a certain scanning line.

[Math. 2]

$$MCI = 1 - \frac{\int\int\int \text{Angiogram}(z, x, t)dzdxdt}{\int\int\int \text{Intensity}(z, x, t)dzdxdt} \quad (2)$$

Here, in Formula (2), Angiogram indicates the MC image, Intensity indicates the intensity image, x and z indicate coordinates, and t indicates a time (frame).

In this case, the ratio increases in the scanning line in which there is an artifact (for example, an unnecessary signal which is not related to the structure of the test substance). As the MCI closer to 1, the clear MC image with no artifact is obtained.

As expressed in Formula (3), the MCI may be a correlation value $\Gamma$ between complex OCT signals at the time of generation of the MC image (see Non-Patent Document 1).

[Math. 3]

$$MCI = \frac{\int R(z, x, t)R^*(z, x, t_0)dzdx}{\sqrt{\int |R(z, x, t)|^2 \, dzdx} \sqrt{\int |R(z, x, t_0)|^2 \, dzdx}} \quad (3)$$

Here, R indicates the complex OCT signal, R* indicates a complex conjugate of R, x and z indicate coordinates, t indicates a time (frame), and t0 indicates a standard time (frame).

In this case, as the correlation value $\Gamma$ is closer to 1, deviation of an eye is smaller. Thus, the clear MC image can be obtained. On the other hand, when an eye moves, the correlation value $\Gamma$ between the complex OCT signals decrease, and thus the MC image becomes unclear.

The MCI may be a correlation value between the intensity images. In this case, a normalized cross-correlation (ZNCC) illustrated in Formula (4) can be used.

[Math. 4]

$$MCI = \frac{\int\int\left\{\left(\left|R(z,x,t)\right| - \frac{\int\int|R(z,x,t)|dzdx}{N}\right)\left(\left|R(z,x,t_0)\right| - \frac{\int\int|R(z,x,t_0)|dzdx}{N}\right)\right\}dzdx}{\sqrt{\int\int\left(\left|R(z,x,t)\right| - \frac{\int\int|R(z,x,t)|dzdx}{N}\right)^2 dzdx \times \int\int\left(\left|R(z,x,t_0)\right| - \frac{\int\int|R(z,x,t_0)|dzdx}{N}\right)^2 dzdx}} \quad (4)$$

Here, R indicates the complex OCT signal, N indicates the number of all pixels, x and z indicate coordinates, and t indicates a time (frame).

In this case, as the value of ZNCC is closer to 1, the correlation is higher (the deviation in the eye is smaller), and thus the clear MC image is obtained. As the value of ZNCC is closer to 0, the correlation is lower, and thus the unclear MC image is obtained.

The CPU 71 may display the MCI corresponding to the depth region designated in the first switch portion 84 in the third display region 83. For example, in a case in which the depth region is switched in the first switch portion 84, the CPU 71 may switch the display of the MCI to correspond to the switched depth region. Of course, the CPU 71 may display a plurality of MCIs corresponding to layers.

In addition to the MCI, the CPU 71 may display, for example, an index indicating clearness of the intensity image or an index indicating clearness of a front observed image of the subject's eye E imaged by the front observation optical system 200 in the third display region 83 (see FIGS. 5A and 5B).

In the confirmation screen 80B illustrated in FIG. 6, for example, a fourth display region 86 is displayed in addition to the second display region 82, the third display region 83, the first switch portion 84, and the second switch portion 85. For example, the fourth display region 86 is a region in which an MC image with a different display magnification from the MC image in the first display region 81 is displayed.

Fourth Display Region

For example, as illustrated in FIG. 6, the CPU 71 displays, in the fourth display region 86, the MC image with a smaller display magnification than the MC image in the first display region 81. In the example of FIG. 6, the CPU 71 displays the front observed image of the subject's eye E imaged by the front observation optical system 200 and the MC image overlapping with the front observed image in the fourth display region 86.

For example, the CPU 71 switches the display magnification of the MC image by switching the confirmation screen between the confirmation screens 80A and 80B according to an operation on the second switch portion 85. For example, the tester can confirm clearness of capillary vessels in the first display region 81 in which the expanded MC image is displayed and confirm the position of the region A1 in which the OCT signal is acquired in accordance with the MC image in the fourth display region. The CPU 71 may expand and display the MC image in another window or may expand and display a selected region of a part of the MC image. The CPU 71 may display the MC images with different display magnifications side by side on one screen.

Of course, the display magnification of the MC images may be set in advance or may be changed to any display magnification.

The tester confirms the quality of the MC data on the confirmation screen 80. For example, the tester switches the depth region of the MC image displayed in the first display region 81 in accordance with the first switch portion 84 and confirms the MC image in a desired depth region. The tester may change the display magnification of the MC images in accordance with the second switch portion 85. The tester may confirm the quality of the MC data with reference to the MCI displayed in the third display region 83.

As described above, for example, the tester confirms the quality of the MC image in accordance with the confirmation screen 80 to determine whether the imaging is skillfully performed. For example, in a case in which the tester determines that the imaging is skillfully performed, the tester presses an OK button 87 in FIGS. 5A and 5B. In a case in which the tester determines that the imaging is not skillfully performed, the tester presses a retry button 88.

(Step S4)

Determining Whether Imaging is Successful

When the retry button 88 is pressed by the tester, for example, the CPU 71 abandons the acquired OCT data (step S5) and images the subject' eye E by the OCT device 10 again (step S1). On the other hand, when the OK button 87 is pressed by the tester, for example, the CPU 71 stores the acquired OCT data in the storage unit 74.

(Step S6)

Displaying Analysis Screen

When the imaging is completed, for example, the CPU 71 may display an analysis screen (not illustrated) on the display unit 75. The analysis screen is, for example, a screen used to analyze the OCT data stored in the storage unit 74 and display an analysis result of the OCT data. For example, the CPU 71 displays the detailed analysis result obtained through an analysis process in which a processing time is long on the analysis screen. The tester confirms the detailed analysis result of the subject's eye E on the analysis screen. For example, the CPU 71 may transition the screen from the confirmation screen 80 to the analysis screen or may transition the screen via another screen. For example, the CPU 71 may display a list screen of imaging results from the confirmation screen 80 and display the analysis screen regarding to the imaging result selected on the list screen.

As described above, when the MC image of a desired depth region of the tester is displayed on the confirmation screen 80, the tester can simply determine the quality of the MC data. Since the tester can determine the quality of the MC data before the completion of the imaging, the tester may interrupt the imaging halfway and may perform re-imaging. Accordingly, a time of the entire imaging is shortened and a burden on the test substance is reduced.

In the OCT signal processing apparatus 1 according to the embodiment, it is possible to easily confirm whether a specific depth region is skillfully imaged more than a case in which only the MC image of all the retina layers may not be confirmed.

In a case in which the SD-OCT is used in the OCT device 10, sensitivity attenuation occurs in some cases. Accordingly, even when the MC image of a shallow depth region is clear, there is a possibility of the MC image in a deep depth region being unclear. In this case, it is difficult to understand that the MC image in the deep depth region is unclear with only the MC image of all retina layers. Accordingly, when the MC image of a partial depth region is displayed as in the embodiment, the tester can individually confirm the MC image of the deep depth region. Therefore, it is possible to easily confirm a defective of the MC image occurring due to the sensitivity attenuation.

Figure 7:
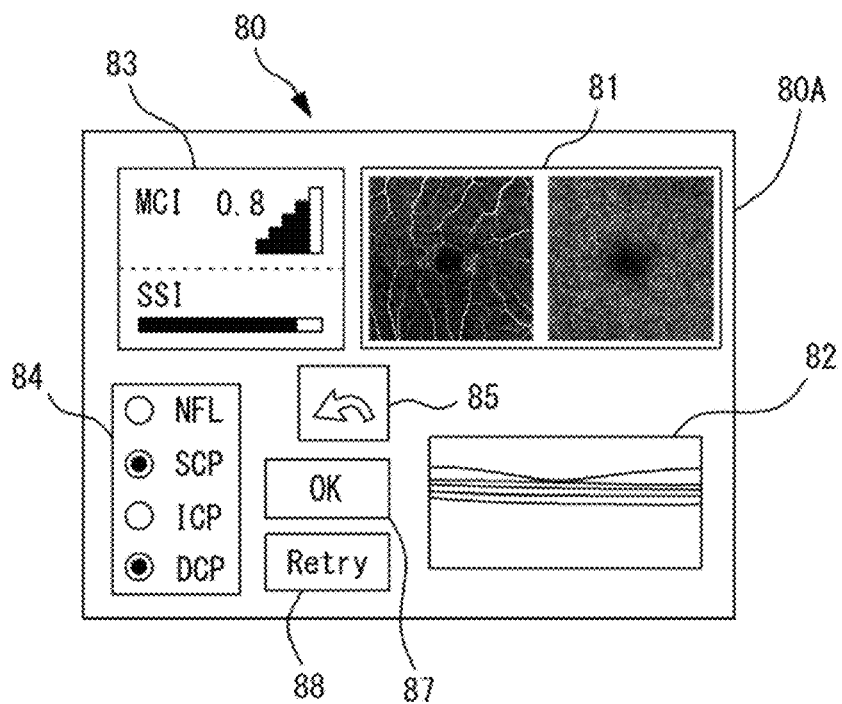
FIG. 7 is a diagram illustrating a modification example of the display screen according to the embodiment.

For example, the CPU 71 may display the plurality of MC images of depth regions of different depths on the confirmation screen 80. For example, as illustrated in FIG. 7, the CPU 71 may display the plurality of MC images in depth regions of different depths such as the SCP and the DCP side by side on the first display region 81. Accordingly, it is possible to determine the quality of the other MC images of the different depths with reference to the MC image of a depth region by which the MC images of different depth regions can be compared.

The CPU 71 may display a 3-dimensional MC image, an MC front image, and an MC image of any blood vessel in the first display region 81. For example, the CPU 71 may display these images side by side in the first display region 81 or may display these images so that the images can be switched. Further, the CPU 71 may display an MC front image and a front image with an intensity of a depth region corresponding to the MC front image side by side in the first display region 81. For the MC image, color display and negative/positive display can be switched. Of course, the MC image may be a still image or a moving image.

The CPU 71 may display the analysis result of the MC image in the first display region 81. For example, the CPU 71 may display a region analysis result such as an analysis result of an area of a foveal avascular zone (FAZ), a shape measurement, or the like or a discrimination result of an artery or a vein so that the region analysis result overlaps with the MC image. The CPU 71 may detect an artifact or the like (for example, a horizontal stripe in a scanning line direction) on the MC image, and may emphasize and display the artifact using an arrow, coloring, or the like. For example, the CPU 71 may prompt re-imaging by detecting an artifact through image processing, the above-described MCI calculation, or the like and emphasizing and displaying a corresponding region on the MC image. The tester can easily determine whether to perform the re-imaging with reference to such an analysis result or the like.

The CPU 71 may sequentially display the MC images from the imaged scanning line. Accordingly, the tester can know the progressive status of the imaging. For example, in a case in which the tester finds an artifact during the imaging, the tester may perform re-imaging.

Setting Depth Region

The CPU 71 may automatically set the depth region of the MC image to be displayed in the first display region 81. For example, the CPU 71 may detect a lesion portion by analyzing the MC data and display the MC image of the depth region containing the detected lesion portion in the first display region 81. For example, the CPU 71 may binarize the MC image and detect a dark region in which no blood vessel is detected as a lesion portion. In this way, by automatically setting the depth region of the MC image based on the detected lesion, it is possible to reduce a labor for switching the depth region to find whether there is a lesion. When the MC image of the depth region considered to be a lesion is displayed, the tester can determine whether to re-image the periphery of the lesion in more detail.

For example, the CPU 71 may automatically set the depth region of the MC image to be displayed in the first display region 81 based on an imaging condition. For example, the CPU 71 may automatically set the depth region of the MC image based on a scanning position (for example, the periphery of a macula or the periphery of a papilla) of the measurement light or a scanning pattern (for example, a raster, a circle, or a cross).

The CPU 71 may automatically set the depth region of the MC image to be displayed in the first display region 81 from medical history data of a patient. For example, the CPU 71 may display the MC image of a certain depth region in which a lesion is generated in the first display region 81 with reference to the medical history data stored in the storage unit 74 or the like. Accordingly, the tester can easily perform a progressive observation of the lesion portion. Of course, the CPU 71 may display the MC image of a reset depth region.

The confirmation screens described above are merely examples and it is not necessary to display all of the foregoing elements (for example, the first display region 81, the second display region 82, the third display region 83, the fourth display region 86, the first switch portion 84, the second switch portion 85, the OK button 87, and the retry button 88). Of course, the CPU 71 may change the configuration of the confirmation screen according to an imaging condition. For example, different confirmation screens may be displayed at the time of macula imaging and the time of papilla imaging. Incidentally, the confirmation screen may be displayed before the processing of the MC image is completed, and the confirmation screen including an image using a part of the MC image which is available at the time of displaying the confirmation screen may be displayed.

What is claimed is:

1. An OCT signal processing apparatus comprising:
   an OCT signal receiver configured to receive a plurality of OCT signals detected by an OCT device based on measurement light radiated to a test substance and reference light, the plurality of OCT signals being temporally different from each other in the same region of the test substance;
   a display;
   a controller configured to:
   process the plurality of OCT signals received by the OCT signal receiver using a Fourier transformation to obtain 3-dimensional motion contrast data;
   extract depth region data from the 3-dimensional motion contrast data, the extracted depth region data representing motion contrast data in a depth region of a part of the test substance;
   display, on the display, a confirmation screen including a motion contrast image based on the extracted depth region data to confirm quality of 3-dimensional motion contrast data obtained by processing the plurality of OCT signals; and display a retry button for performing re-imaging to obtain new 3-dimensional motion contrast data on the confirmation screen.

2. The OCT signal processing apparatus according to claim 1, wherein the controller displays the plurality of motion contrast images generated for the depth region data extracted in the plurality of depth regions in which depths are different on the confirmation screen in such a manner that the motion contrast images are switchable.

3. The OCT signal processing apparatus according to claim 1, wherein the controller extracts the pieces of depth region data in the plurality of depth regions in which depths are different, and arranges and displays the plurality of motion contrast images generated for the plurality of pieces of extracted depth region data on the confirmation screen.

4. The OCT signal processing apparatus according to claim 1, wherein the controller detects a lesion based on the 3-dimensional motion contrast data and displays the motion contrast image in the depth region containing the detected lesion on the confirmation screen.

5. The OCT signal processing apparatus according to claim 1, wherein the controller specifies the depth region based on patient information of the test substance and displays the motion contrast image in the specified depth region on the confirmation screen.

6. The OCT signal processing apparatus according to claim 1, wherein the controller specifies the depth region based on an imaging condition when the test substance is imaged by the OCT device, and displays the motion contrast image in the specified depth region on the confirmation screen.

7. The OCT signal processing apparatus according to claim 1, wherein the controller switches a display magnification of the motion contrast image and displays the motion contrast image on the confirmation screen based on the switched display magnification.

8. The OCT signal processing apparatus according to claim 1, wherein the controller arranges and displays the plurality of motion contrast images in which display magnifications are mutually different on the confirmation screen.

9. The OCT signal processing apparatus according to claim 1, wherein the controller sequentially displays the motion contrast images on the confirmation screen from a pixel line corresponding to the acquired scanned line.

10. The OCT signal processing apparatus according to claim 1, wherein the controller displays an index for evaluating the 3-dimensional motion contrast data on the confirmation screen.

11. The OCT signal processing apparatus according to claim 1, wherein the controller calculates a plurality of indexes for each of the plurality of pieces of depth region data and displays at least one of the plurality of calculated indexes on the confirmation screen.

12. The OCT signal processing apparatus according to claim 1, wherein the controller displays an analysis result in the motion contrast image displayed on the confirmation screen.

13. The OCT signal processing apparatus according to claim 1, wherein the motion contrast image is an enface image based on the depth region data.

14. The OCT signal processing apparatus according to claim 1, wherein
the OCT device detects the OCT signal based on the measurement light and the reference light radiated to a fundus of a subject's eye, and
the controller extracts the depth region data in the depth region of a part of the fundus from the 3-dimensional motion contrast data.

15. The OCT signal processing apparatus according to claim 1, wherein
the confirmation screen includes a first button and a second button,
when the first button is operated by a tester, the controller abandons the 3-dimensional motion contrast data and acquire a plurality of new OCT signals, and
when the second button is operated by a tester, the controller stores the 3-dimensional motion contrast data in a memory.

16. A non-transitory computer readable recording medium storing an OCT signal processing program, when executed by a processor of an OCT signal processing apparatus including an OCT signal receiver configured to receive a plurality of OCT signals detected by an OCT device based on measurement light radiated to a test substance and reference light and a display, the plurality of OCT signals being temporally different from each other in the same region of the test substance, causing the OCT signal processing apparatus to execute:
processing the plurality of OCT signals received by the OCT signal receiver using a Fourier transformation to obtain 3-dimensional motion contrast data;
extract depth region data from the 3-dimensional motion contrast data, the extracted depth region data representing motion contrast data in a depth region of a part of the test substance;
display, on the display, a confirmation screen including a motion contrast image based on the extracted depth region data to confirm quality of 3-dimensional motion contrast data obtained by processing the plurality of OCT signals; and
display a retry button for performing re-imaging to obtain new 3-dimensional motion contrast data on the confirmation screen.

17. An OCT apparatus comprising:
an OCT optical system including a scanning unit configured to scan a test substance with measurement light, the OCT optical system acquiring a plurality of OCT signals based on measurement light scanned on a test substance by a scanning unit and reference light;
a display; and
a controller configured, when a release signal for starting imaging of the test substance by OCT optical system is received, to:
acquire the plurality of OCT signals which are temporally different from each other in the same region by controlling the scanning unit;
process the plurality of OCT signals using a Fourier transformation to obtain 3-dimensional motion contrast data;
extract depth region data from the 3-dimensional motion contrast data, the extracted depth region data representing motion contrast data in a depth region of a part of the test substance;
display a confirmation screen including the motion contrast data on the display based on the extracted depth region data to confirm quality of the 3-dimensional motion contrast data; and
display a retry button for performing re-imaging to obtain new 3-dimensional motion contrast data on the confirmation screen.

* * * * *